United States Patent [19]

Hughes et al.

[11] Patent Number: 5,157,122
[45] Date of Patent: Oct. 20, 1992

[54] PROCESS FOR THE PREPARATION OF 3-UNSUBSTITUTED INDOLES USING METHANE SULFONIC ACID AS AN ADDITIONAL CATALYST

[75] Inventors: David L. Hughes, Old Bridge; Dalian Zhao, Scotch Plains, both of N.J.

[73] Assignee: Merck & Co., Inc., Rahway, N.J.

[21] Appl. No.: 642,778

[22] Filed: Jan. 18, 1991

[51] Int. Cl.$^5$ .................. C07D 209/10; C07D 403/12
[52] U.S. Cl. .................................. 546/176; 546/178; 548/502
[58] Field of Search ................. 548/502; 546/178, 176

[56] References Cited

PUBLICATIONS

P. E. Eaton et al., Phosphorous Pentoxide–Methanesulfonic Acid, *J. Org. Chem.* 38, 4071 (1973).
A. Guy and J. P. Guette, Utilization of Polyphosphoric Acid *Synthesis*, 1980, 222.
H. Illy and L. Funderburk, Fisher Indole Syn. Direction of Cyclization, *J. Org. Chem.*, 33, 4283 (1968).
M. H. Palmer and P. S. McIntyre, Fischer Indole Syn. Unsymmetrical Ketones, *J. Chem. Soc. (B), 1969, 446*.

Primary Examiner—David B. Springer
Attorney, Agent, or Firm—Gabriel Lopez; Joseph F. DiPrima; David A. Muthard

[57] ABSTRACT

An indole having the formula I:

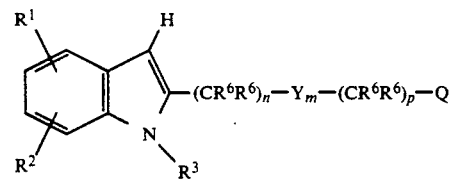

is prepared by a Fischer-Indole reaction employing a mixture of phosphorous pentoxide and methane sulfonic acid as an acid catalyst. The reaction, which is optionally run in a co-solvent, provides 3-unsubstituted indoles in high yields with high regioselectivity. The indole thus prepared is an intermediate in the synthesis of leukotriene biosynthesis-inhibitors.

16 Claims, No Drawings

PROCESS FOR THE PREPARATION OF 3-UNSUBSTITUTED INDOLES USING METHANE SULFONIC ACID AS AN ADDITIONAL CATALYST

BACKGROUND OF THE INVENTION

The Fischer indole reaction provides a versatile and convergent route to a wide variety of indoles. However, when the ketone component of the reaction has two enolizable sites, regiocontrol is often a problem. In 1902 Plancher and Bonavia (Gazz. Chim. Ital. II, 32, 414 (1902)) published general rules governing the direction of indolization of unsymmetrical ketone arylhydrazones, the gist of which were that hydrazones made from methyl alkyl ketones A give 3-substituted-2-methylindoles B as the major products (eq. 1) and that dialkyl ketones give mixtures of products.

EQUATION 1

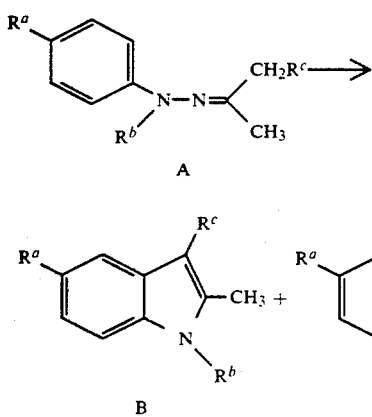

In the intervening years many examples have supported the conclusion that methyl alkyl ketones provide the 3-substituted-2-methylindoles B as the sole or major product (B. Robinson, "The Fischer Indole Synthesis," Wiley:New York, 1982, pp. 241-250).

F. A. Trofinov, et al. (Chem. Het. Comps., 15, 63 (1979) and citations therein) have disclosed that a thioether group may be used to direct the regiochemistry of the indolization and subsequently removed to provide the 3-unsubstituted indole.

H. Illy and L. Funderburk (J. Org. Chem., 11, 4283 (1968)) have disclosed studies in which they varied the strength of the acid catalysts employed in the reaction illustrated hereinbelow (D: $R^a = R^b = H$, $R^c = R^d = CH_3$). They disclose that the greater ratio of compounds F:E are obtained when strongly acidic conditions are employed and the highest ratio was observed when 5 molar equivalents of polyphosphoric acid (PPA) were employed with toluene as a solvent.

EQUATION 2

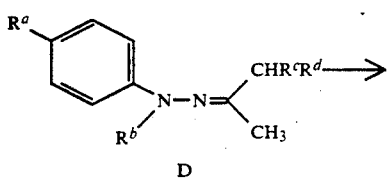

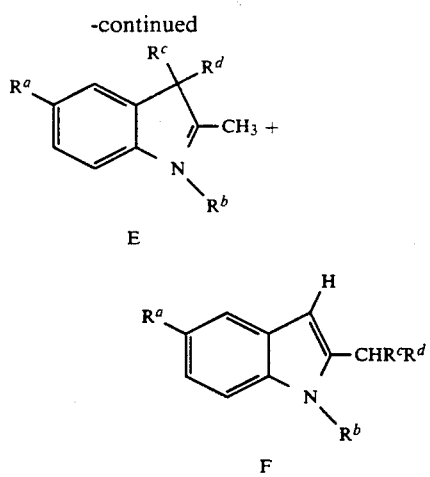

M. H. Palmer and P. S. McIntyre (J. Chem. Soc. (B), 446 (1969)) have disclosed studies similar to Illy and Funderburk using various acid catalysts and several phenylhydrazones. They disclose that the 3-unsubstituted product is obtained exclusively when D ($R^a = R^b = H$, $R^c = R^d = CH_3$) is reacted in 70% sulfuric acid in aqueous ethanol. When D ($R^a = R^b = R^c = H$, $R^d = CH_3$) is reacted under similar conditions, the two products E and F are formed in equal amounts.

P. E. Eaton, et al. (J. Org. Chem., 23, 4071 (1973)) disclose a new reagent, a 1:10 by weight solution of phosphorous pentoxide in methane sulfonic acid which is an effective substitute for polyphosphoric acid. They cite greater ease of handling, increased solubility of organic compounds in the reagent and more convenient workup procedures as reasons for the attractiveness of the new reagent. They also state that in terms of relative rate, product distribution and yield, the new reagent mimics PPA in the selected examples they studied.

European Patent Application 166,591 and 275,667 disclose a series of indole-based compounds with activity as prostaglandin antagonists and inhibitors of leukotriene biosynthesis respectively.

A number of N-acyl derivatives of indole-3-acetic acid are described as potential anti-inflammatory agents by Biniecki, et al., Chem. Ab., Vol. 98, 197936 (1983), by Pakula, et al., Chem. Ab., Vol. 105, 190835 (1986), and in British Pat. Spec. 1,228,848.

It is an object of the instant invention to provide a improved process for the preparation of 3-unsubstituted indoles by a Fischer Indole reaction in the presence of a mixture of phosphorous pentoxide and methane sulfonic acid. It is also an object to provide a process wherein a co-solvent is optionally employed.

It is also an object of the instant invention to provide a process for the preparation of 3-unsubstituted indoles having increased product yield and regiochemical control, relative to processes known in the art and described hereinabove, in the case where the ketone component of the hydrazone has two enolizable sites.

It is a further object of the instant invention to provide a novel process for the preparation of 3-unsubstituted indoles which are utilized as intermediates in the syntheses of leukotriene biosynthesis inhibitors.

SUMMARY OF THE INVENTION

The present invention provides a novel process for the preparation of a compound of the formula I:

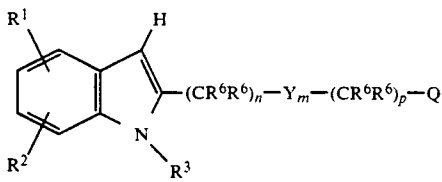

wherein:
R[1] is hydrogen, halogen, lower alkyl, lower alkenyl, lower alkynyl, —CF$_3$, —CN, —NO$_2$, —N$_3$, —C(OH)R[6]R[6], —CO$_2$R[7], —SR[8], —S(O)R[8], —S(O)$_2$R[8], —S(O)$_2$NR[9]R[9], —OR[9], —NR[9]R[9], —C(O)R[10], —(CH$_2$)$_r$R[18] or

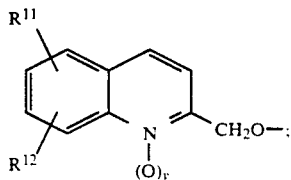

R[2], R[5], R[11] and R[12] are independently hydrogen, halogen, lower alkyl, lower alkenyl, lower alkynyl, —CF$_3$, —CN, —NO$_2$, —N$_3$, —C(OH)R[6]R[6], —CO$_2$R[7], —SR[8], —S(O)R[8], —S(O)$_2$R[8], —S(O)$_2$NR[9]R[9], —OR[9], —NR[9]R[9], —C(O)R[10] or —(CH$_2$)$_r$R[18];

R[3] is hydrogen or X[3]—R[4];

R[4] is alkyl, alkenyl, —(CH$_2$)$_u$Ph(R[5])$_2$ or —(CH$_2$)$_u$Th(R[5])$_2$;

each R[6] is independently hydrogen or lower alkyl, or two R[6]'s on same carbon atom are joined to form a cycloalkyl ring of 3 to 6 carbon atoms;

R[7] is hydrogen, lower alkyl or —CH$_2$R[18];

R[8] is —CF$_3$ or R[13];

R[9] is hydrogen, —C(O)R[10], R[13], or two R[9]'s on the same nitrogen may be joined to form a monocyclic heterocyclic ring of 4 to 6 atoms containing up to 2 heteroatoms chosen from O, S or N;

R[10] is hydrogen, —CF$_3$, lower alkyl, lower alkenyl, lower alkynyl or —(CH$_2$)$_r$R[18];

R[13] is lower alkyl or —(CH$_2$)$_r$R[18];

R[14] is —(CH$_2$)$_s$—C(R[15]R[15])—(CH$_2$)$_s$—R[16] or —CH$_2$C(O)NR[9]R[9];

R[15] is hydrogen or lower alkyl;

R[16] is a) a monocyclic or bicyclic heterocyclic ring containing from 3 to 9 nuclear carbon atoms and 1 or 2 nuclear hetero-atoms selected from N, S or O and with each ring in the heterocyclic radical being formed of 5 or 6 atoms, or b) the radical W—R[17];

R[17] is alkyl or —C(O)R[20];

R[18] is phenyl substituted with 1 or 2 R[19] groups;

R[19] is hydrogen, halogen, lower alkyl, lower alkoxy, lower alkylthio, lower alkylsulfonyl, lower alkylcarbonyl, —CF$_3$, —CN, —NO$_2$ or —N$_3$;

R[20] is alkyl, cycloalkyl, or monocyclic monoheterocyclic ring;

R[21] is the residual structure of a standard amino acid, or R[15] and R[21] attached to the same N can cyclize to form a proline residue;

m is 0 to 1;
n is 1 to 3;
p is 1 to 3 when m is 1;
p is 0 to 3 when m is 0;
r is 0 to 2;
s is 0 to 3;
t is 0 to 2;
u is 0 to 3;
v is 0 or 1;
W is O, S or NR[9];
X[1] is O or NR[9];
X[2] is C(O), CR[6]R[6], S, S(O), or S(O)$_2$;
X[3] is C(O), CR[6]R[6], S(O)$_2$ or a bond;
Y is X[1] or X[2];
Q is hydrogen, —CO$_2$R[7], —C(O)NHS(O)$_2$R[8], —NHS(O)$_2$R[8], —S(O)$_2$NHR[9]—C(O)NR[9]R[9], —CO$_2$R[14], —C(O)NR[15]R[21], —CH$_2$OH, or 1H- or 2H-tetrazol-5-yl;

comprising the step of treating the hydrazone compound of the Formula II:

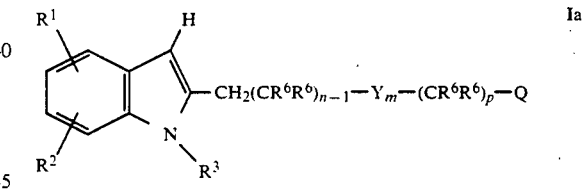

wherein R[1], R[2], R[3], R[6], Y, Q, m, n and p are as defined hereinabove;

with a catalyst mixture comprising phosphorous pentoxide and methane sulfonic acid in a ratio in the range of 1:2 to 1:4 and, optionally, in the presence of a co-solvent, in a ratio in the range of 1:1 to 1:10 relative to the catalyst mixture.

An embodiment of the process of the instant invention is a novel process for the preparation of the formula Ia:

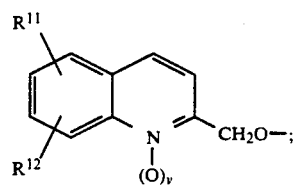

wherein:
R[1] is hydrogen, halogen, lower alkyl, lower alkenyl, lower alkynyl, —CF$_3$, —CN, —NO$_2$, —N$_3$, —C(OH)R[6]R[6], —CO$_2$R[7], —SR[8], —S(O)R[8], —S(O)$_2$R[8], —S(O)$_2$NR[9]R[9], —OR[9], —NR[9]R[9], —C(O)R[10], —(CH$_2$)$_r$R[18] or

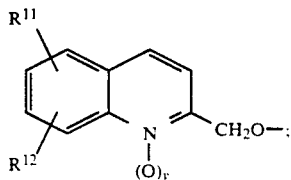

R[2], R[5], R[11] and R[12] are independently hydrogen, halogen, lower alkyl, lower alkenyl, lower alkynyl, —CF$_3$, —CN, —NO$_2$, —N$_3$, —C(OH)R[6]R[6], —CO$_2$R[7], —SR[8], —S(O)R[8], —S(O)$_2$R[8], —S(O)$_2$NR[9]R[9], —OR[9], —NR[9]R[9], —C(O)R[10] or —(CH$_2$)$_r$R[18];

R[3] is hydrogen or X[3]—R[4];

$R^4$ is alkyl, alkenyl, —$(CH_2)_uPh(R^5)_2$ or —$(CH_2)_uTh(R^5)_2$;

each $R^6$ is independently hydrogen or lower alkyl, or two $R^6$'s on same carbon atom are joined to form a cycloalkyl ring of 3 to 6 carbon atoms;

$R^7$ is hydrogen, lower alkyl or —$CH_2R^{18}$;

$R^8$ is —$CF_3$ or $R^{13}$;

$R^9$ is hydrogen, —$C(O)R^{10}$, $R^{13}$, or two $R^9$'s on the same nitrogen may be joined to form a monocyclic heterocyclic ring of 4 to 6 atoms containing up to 2 heteroatoms chosen from O, S or N;

$R^{10}$ is hydrogen, —$CF_3$, lower alkyl, lower alkenyl, lower alkynyl or —$(CH_2)_rR^{18}$;

$R^{13}$ is lower alkyl or —$(CH_2)_rR^{18}$;

$R^{14}$ is —$(CH_2)_s$—$C(R^{15}R^{15})$—$(CH_2)_s$—$R^{16}$ or —$CH_2$—$C(O)NR^9R^9$;

$R^{15}$ is hydrogen or lower alkyl;

$R^{16}$ is a) a monocyclic or bicyclic heterocyclic ring containing from 3 to 9 nuclear carbon atoms and 1 or 2 nuclear hetero-atoms selected from N, S or O and with each ring in the heterocyclic radical being formed of 5 or 6 atoms, or b) the radical W—$R^{17}$;

$R^{17}$ is alkyl or —$C(O)R^{20}$;

$R^{18}$ is phenyl substituted with 1 or 2 $R^{19}$ groups;

$R^{19}$ is hydrogen, halogen, lower alkyl, lower alkoxy, lower alkylthio, lower alkylsulfonyl, lower alkylcarbonyl, —$CF_3$, —CN, —$NO_2$ or —$N_3$;

$R^{20}$ is alkyl, cycloalkyl, or monocyclic monoheterocyclic ring;

$R^{21}$ is the residual structure of a standard amino acid, or $R^{15}$ and $R^{21}$ attached to the same N can cyclize to form a proline residue;

m is 0 to 1;
n is 1 to 3;
p is 1 to 3 when m is 1;
p is 0 to 3 when m is 0;
r is 0 to 2;
s is 0 to 3;
t is 0 to 2;
u is 0 to 3;
v is 0 or 1;
W is O, S or $NR^9$;
$X^1$ is O or $NR^9$,
$X^2$ is C(O), $CR^6R^6$, S, S(O), or $S(O)_2$;
$X^3$ is C(O), $CR^6R^6$, $S(O)_2$ or a bond;
Y is $X^1$ or $X^2$;
Q is hydrogen, —$CO_2R^7$, —$C(O)NHS(O)_2R^8$, —$NHS(O)_2R^8$, —$S(O)_2NHR^9$—$C(O)NR^9R^9$, —$CO_2R^{14}$, —$C(O)NR^{15}R^{21}$, —$CH_2OH$, or 1H- or 2H-tetrazol-5-yl;

comprising the step of treating the hydrazone compound of the Formula IIa:

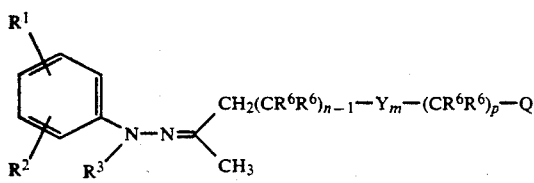

IIa wherein $R^1$, $R^2$, $R^3$, $R^6$, Y, Q, m, n and p are as defined hereinabove;

with a catalyst mixture comprising phosphorous pentoxide and methane sulfonic acid in a ratio in the range of 1:2 to 1:40 and, optionally, in the presence of a co-solvent, in a ratio in the range of 1:1 to 1:10 relative to the catalyst mixture.

One embodiment of the process of the instant invention is that in which a co-solvent is present.

Another embodiment of the process of the instant invention is that in which a co-solvent is not present.

Another embodiment of the process of the instant invention is that in which:

$R^1$ is fluorine, lower alkyl or

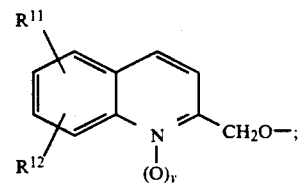

$R^2$, $R^{11}$ and $R^{12}$ are hydrogen;
$R^3$ is $X^3$—$R^4$;
$R^4$ is —$(CH_2)_uPh(R^5)_2$;
$R^5$ is hydrogen or halogen;
m is 0;
n is 1 to 3;
u is 1 in $R^4$;
v is 0;
Q is hydrogen or —$CO_2R^{12}$; and the remaining substituents are as defined for Formula I;
the ratio of phosphorous pentoxide to methane sulfonic acid is 1:9 to 1:35.

A further embodiment is a process wherein dichloromethane is employed as the co-solvent.

A further embodiment is a process wherein sulfolane is employed as the co-solvent.

A more preferred embodiment of the process of the instant invention is that in which a co-solvent is present in a ratio range of 1:1 to 1:3 relative to the catalyst mixture.

DEFINITIONS

The following abbreviations have the indicated meanings:

Me=methyl
Bz=benzyl
Ph=phenyl
t-Bu=tert-butyl
i-Pr=isopropyl
c-$C_6H_{11}$=cyclohexyl
c-Pr=cyclopropyl
c-=cyclo
Ac=acetyl
Tz=5-tetrazolyl
Th=2- or 3-thienyl
c-$C_5H_9$=cyclopentyl
1-Ad=1-adamantyl.

Alkyl, alkenyl, and alkynyl are intended to include linear, branched, and cyclic structures and combinations thereof.

As used herein, the term "alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, cyclododecyl, adamantyl, and the like.

As used herein, the term "lower alkyl" includes those alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like. The preferred lower alkyl groups are methyl, ethyl, propyl and butyl.

The term "cycloalkyl" refers to a hydrocarbon ring having from 3 to 7 carbon atoms. Examples of cycloalkyl groups or rings are cyclopropyl, cyclopentyl, cycloheptyl and the like. When two $R^6$'s are joined to form a cycloalkyl ring the preferred cycloalkyl rings are cyclopentyl and cyclohexyl.

"Lower alkenyl" groups include those alkenyl groups of 2 to 7 carbon atoms. Examples of lower alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl and the like.

"Lower alkynyl" groups include those alkynyl groups of 2 to 7 carbon atoms. Examples of lower alkynyl groups include ethynyl, propargyl, 3-methyl-1-pentynyl, 2-heptynyl and the like.

As used herein, the term "lower alkoxy" includes those alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

The term "monocyclic monoheterocyclic ring" which defines $R^{20}$ includes those monocyclic groups of 5 to 7 members containing only 1 heteroatom selected from N, S or O in the ring. Examples include tetrahydrofuran, tetrahydrothiophene, pyrrolidine, piperidine, tetrahydropyran, and the like.

The term "monocyclic or bicyclic heterocyclic ring" which defines $R^{16}$ may be 2,5-dioxo-1-pyrrolidinyl, (3-pyridinylcarbonyl) amino, 1,3-dihydro-1,3-dioxo-2H-isoindol-2-yl, 1,3-dihydro-2H-isoindol-2-yl, 2,4-imidazolinedion-1-yl, 2,6-piperidinedion-1-yl, 2-imidazolyl, 2-oxo-1,3-dioxolen-4-yl, piperidin-1-yl, morpholin-1-yl, piperazin-1-yl and the like.

The point of attachment of any heterocyclic ring may be at any free valence of the ring.

The term standard amino acid is employed to include the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine. (See F. H. C. Crick, Symposium of the Society for Experimental Biology, 1958 (12) p. 140.)

It is understood that $R^{11}$ and $R^{12}$ may be located at any of positions 3,4,5,6,7 or 8 of the quinoline ring.

As used herein the term "lower alkylthio" includes those alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies $-SCH_2CH_2CH_3$.

The terms $Ph(R^5)_2$ and $Th(R^5)_2$ indicate a phenyl or thienyl group substituted with two $R^5$ substituents.

Halogen includes F, Cl, Br, and I.

It is intended that the definitions of any substituent (e.g., $R^9$, $R^{11}$, $R^{12}$, $Ph(R^5)_2$, etc.) in a particular molecule be independent of its definitions elsewhere in the molecule. Thus, $-NR^9R^9$ represents $-NHH$, $-NHCH_3$, $-NHC_6H_5$, etc.

The monocyclic heterocyclic rings formed when two $R^9$ groups join through N include pyrrolidine, piperidine, morpholine, thiamorpholine, piperazine, and N-methylpiperazine.

The prodrug esters of Q (i.e., when $Q=CO_2R^{17}$) are intended to include the esters such as are described by Saari et al., J. Med. Chem., 21, No. 8, 746–753 (1978), Sakamoto et al., Chem. Pharm. Bull., 32, No. 6, 2241–2248 (1984) and Bundgaard et al., J. Med. Chem., 30, No. 3, 451–454 (1987).

As used herein, the term "co-solvent" includes dichloromethane, sulfolane, toluene, acetonitrile and the like. Of course, one skilled in the art will recognize that any "aqueous solvents" are incompatible with the disclosed reaction. The preferred co-solvents are dichloromethane and sulfolane.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The indole compound I produced by the process of the present invention is useful per se as a synthetic intermediate which leads directly or indirectly to an indole leukotriene biosynthesis inhibitor. It is understood that the compound of formula I may be further modified and that such modifications may lead to a leukotriene biosynthesis inhibitor, such as that disclosed in U.S. patent application Ser. Nos. 397,144 and 552,300. Possible modification processes are disclosed in the cited U.S. Patent Applications, but are not meant to be limiting.

DETAILED DESCRIPTION OF THE INVENTION

The following synthetic schemes illustrate reaction sequences in which the process of the instant invention is employed. In all of the schemes at least one $CR^6R^6$, that one which is α to the imine in the hydrazone, is a methylene ($CH_2$) group. It is understood that these schemes are meant to be illustrative and are not limiting, and that the process of the instant invention will produce similarly excellent yields of 3-unsubstituted indole products when the α $CR^6R^6$ is not a methylene group. However, since one of the advantages of the process of the instant invention is the high degree of regioselectivity afforded when the hydrazone undergoing the reaction has two enolizable centers (i.e. the α $CR^6R^6$ is a methylene), schemes and examples have been chosen to illustrate such an advantage.

Synthetic Scheme 1 illustrates the sequence in which the process of the instant invention is employed. The various substituents and variables $R^1$, $R^2$, $R^3$, $R^6$, Y, Q, n, m and p are defined hereinabove.

It will be apparent to one skilled in the art that the various functional groups ($R^1$, $R^2$, Y, Q, etc.) must be chosen so as to be compatible with the chemistry being carried out. Such compatibility can often be achieved by protecting groups, or by specific variations in the sequence of the reactions.

SCHEME 1

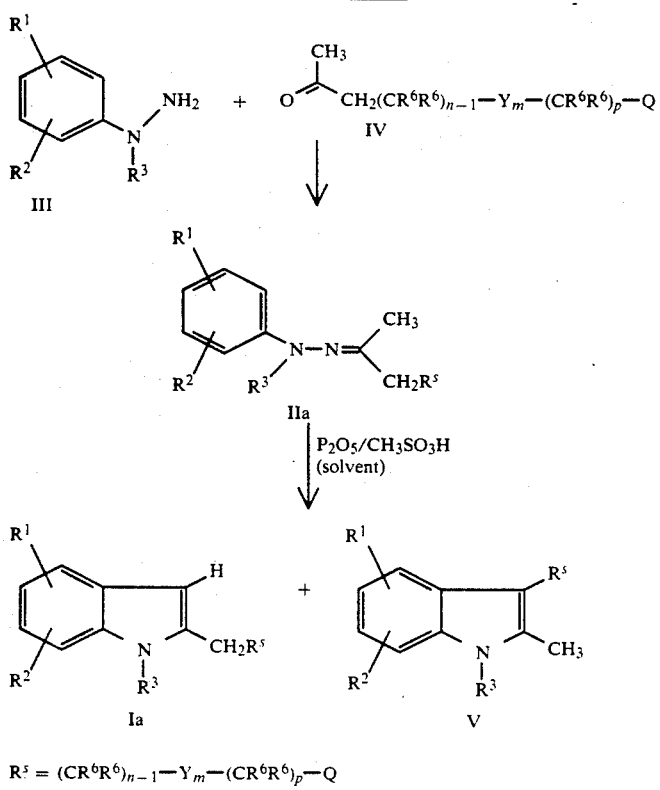

$R^5 = (CR^6R^6)_{n-1} - Y_m - (CR^6R^6)_p - Q$

The steps for preparing the substituted phenylhydrazine III are well known in the art (see for example EP 0 166 591). The methyl ketone IV may be commercially available or may be prepared by synthetic steps well known in the art.

In words relative to the equations, the substituted phenylhydrazine III is reacted with the methyl ketone IV in the presence of a suitable catalyst, such as acetic acid, in a suitable solvent, such as toluene, for a period of time and at a temperature sufficient to produce the hydrazone IIa.

The hydrazone IIa is then treated with a mixture of phosphorous pentoxide and methane sulfonic acid, in an amount, such as 25 molar equivalents, sufficient to produce indole Ia; optionally in a suitable co-solvent, such as methylene chloride, sulfolane, toluene, and the like, at a temperature and for a period of time sufficient to produce indole Ia. Subsequent isolation provided indole Ia in a mixture which contains the isomer V and other minor impurities in negligible amounts. The indole Ia may be purifed by recrystallization or may be used as is in a subsequent modification.

Scheme 2 illustrates a sequence in which the process of the instant invention is employed in the synthesis of leukotriene biosynthesis inhibitors. Such inhibitors have been disclosed in U.S. patent application Ser. Nos. 397,144 and 552,300, filed Aug. 22, 1989, and Jul. 18, 1990, respectively. This scheme is illustrative and is not meant to be limiting.

SCHEME 2

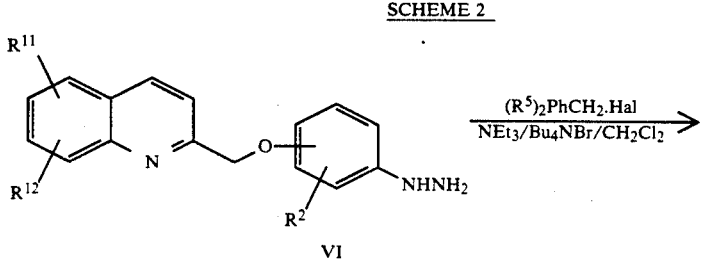

SCHEME 2

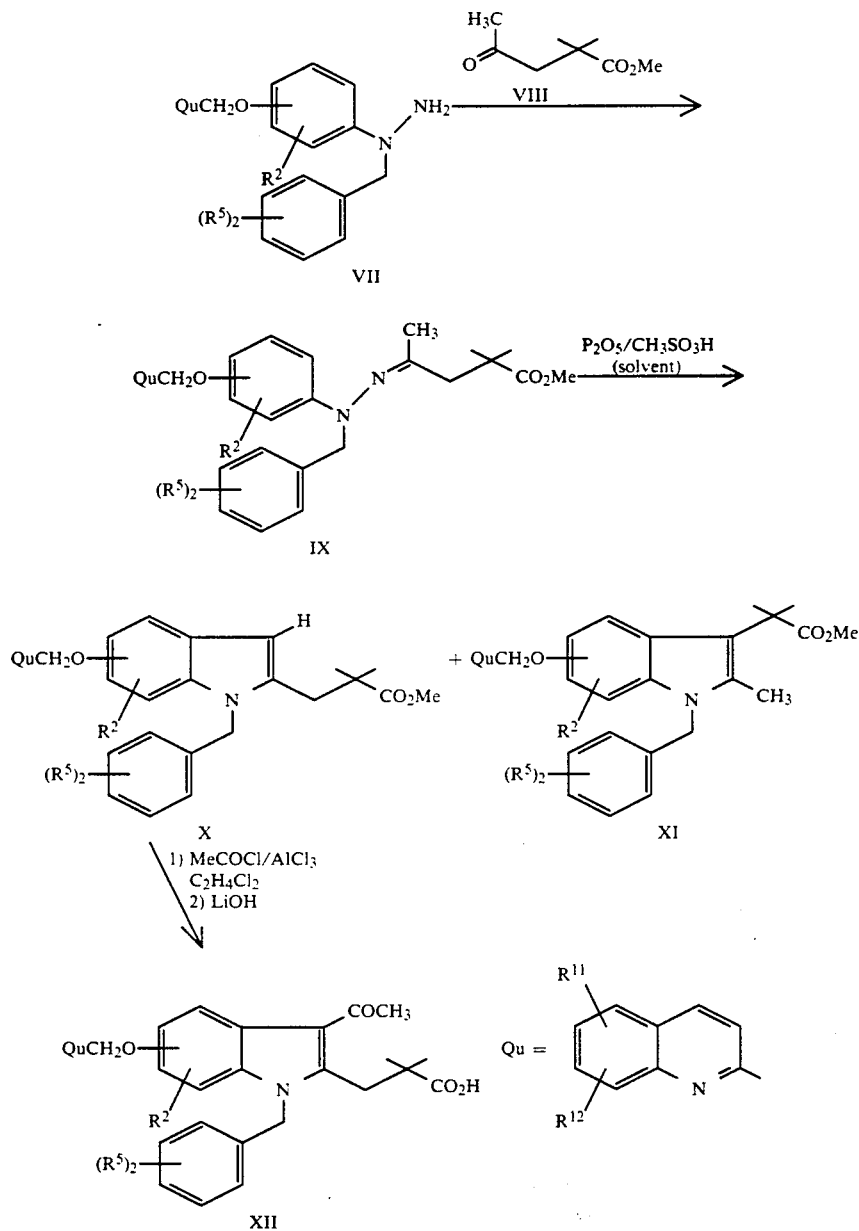

The benzyl phenylhydrazine starting material VII is prepared as described in EP 166,591 (17102 IA) and the ketone VIII is prepared as described in EP 166,591 and EP 275,667 (17496 IA).

In words relative to the equation, the benzyl(-quinolylmethoxyphenyl)hydrazine VII is reacted with the ketone VIII in the presence of an acid catalyst, such as acetic acid and the like, in a suitable solvent, such as toluene and the like. The phenylhydrazine then undergoes the Fischer Indole Synthesis by treatment with a mixture of phosphorous pentoxide and methane sulfonic acid, optionally in a solvent, such as methylene chloride, sulfolane and the like, for a time period and at a temperature sufficient to provide the indole product X. This reaction may also produce a slight amount of the indole XI, which may be readily removed during the purification of indole X. Friedel Crafts reaction of the indole X with an aliphatic acid chloride, such as acetyl chloride and the like, and a suitable Lewis acid, such as aluminum chloride and the like, introduces the acyl substituent into the 3-position of the indole ring. The resulting ester is hydrolyzed by base to yield XII, a leukotriene biosynthesis inhibitor.

SCHEME 3

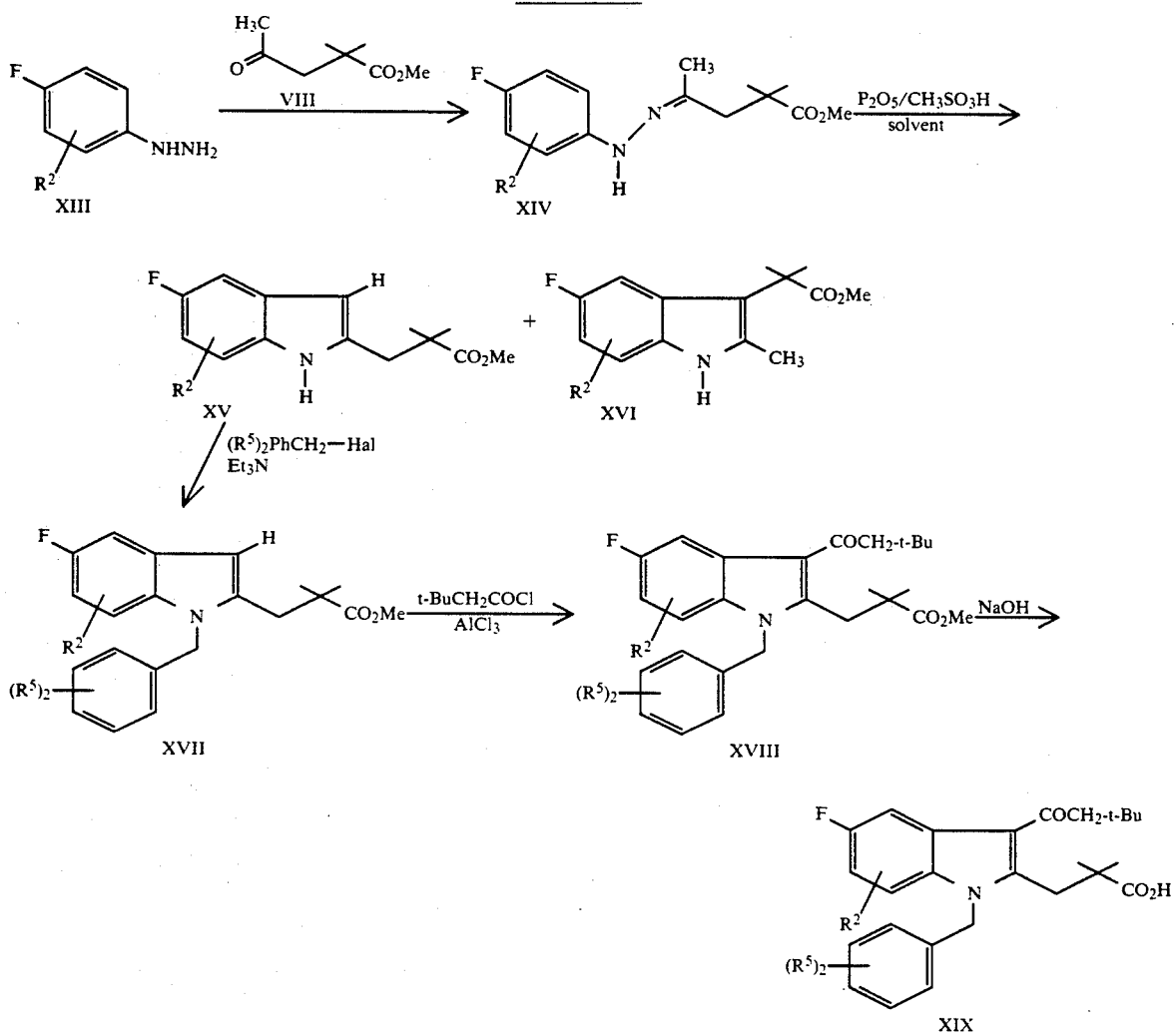

The starting fluoro phenylhydrazine XIII is either commercially available or is described in the chemical literature. The benzyl halide, $(R^5)_2PhCH_2$—Hal, is readily prepared and many such compounds are described in the prior art, such as U.S. Pat. No. 4,808,608 (17323IB)). Hal in $(R^5)_2PhCH_2$—Hal represents Cl, Br or I.

In words relative to the equation, the phenylhydrazine XIII is reacted with the ketone VIII in the presence of an acid catalyst, such as acetic acid and the like, in a suitable solvent, such as toluene and the like. The phenylhydrazone XIV then undergoes the Fischer Indole Synthesis by treatment with a mixture of phosphorous pentoxide and methane sulfonic acid, optionally in a solvent, such as methylene chloride, sulfolane and the like, for a time period and at a temperature sufficient to provide the indole product XV. This reaction may also produce a slight amount of the indole XVI, which may be readily removed during the purification of indole XV. The indole is benzylated by reacting it with a suitably substituted benzyl halide in the presence of a suitable organic base, such as triethylamine, diisopropylethylamine and the like, in a suitable solvent, such as acetonitrile and the like, to provide the indole XVII. Friedel Crafts reaction of the indole XVII with an aliphatic acid chloride, such as t-butylacetyl chloride and the like, and a suitable Lewis acid, such as aluminum chloride and the like, provides the indole XVIII, which is subsequently hydrolyzed to provide indole XIX, a leukotriene biosynthesis inhibitor.

The invention is further defined by reference to the following examples, which are intended to be illustrative and not limiting. The examples demonstrate that the process of the instant invention, illustrated by Example 1, Methods A, B, and C and Examples 2–11, provide superior yields and regiochemical ratios of the 3-unsubstituted indole products when compared with processes currently known in the art (as illustrated in the Background of the Invention and by Example 1, Method D, and in Table 1). All temperatures are in degrees Celsius.

EXAMPLE 1

Preparation of methyl 3-[N-(p-chlorobenzyl)-5-(quinolin-2-ylmethoxy)indol-2-yl]-2,2-dimethylpropanoate

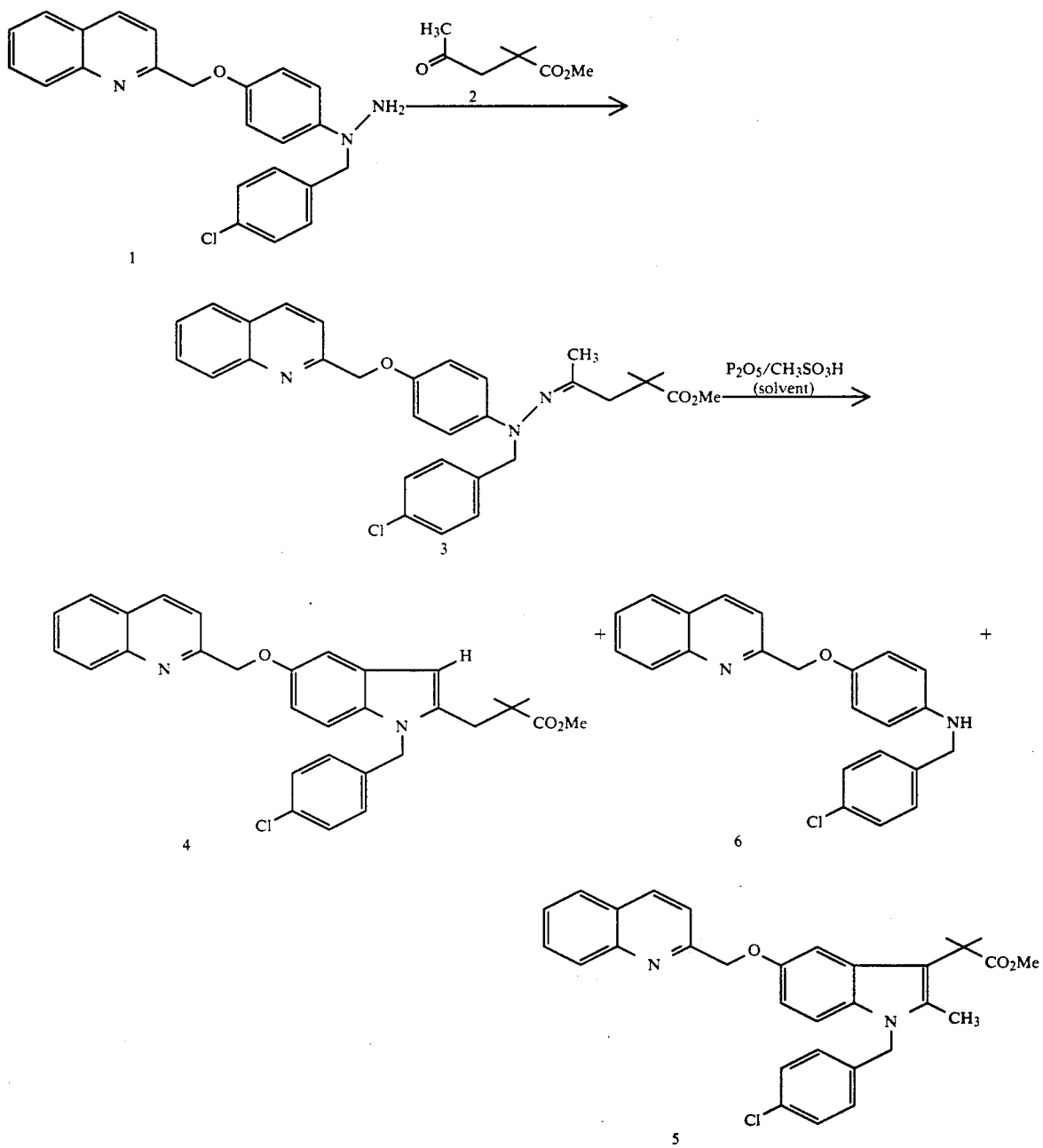

Step A

Preparation of the Hydrazone 3

To a 250 mL round bottomed flask were added 1-(4-chlorobenzyl)-1-[4-(2-quinolymethoxy)phenyl]hydrazine 1 (10.11 g, 25.4 mmol), methyl 2,2-dimethyl-4-oxopentanoate 2 (4.50 g, 28.5 mmol), 4 Å sieves (7.0 g), and toluene (100 ml). The mixture was cooled to 0° C. and acetic acid (2.91 g, 48.5 mmol) was added. The reaction was stirred for 6 hours at 0° C. and 15 hours at 21° C. At the end of the age, HPLC analysis indicated 0.8% unreacted hydrazine, and 92 area % hydrazone 3.

The reaction mixture was filtered and the cake of sieves was washed with 2×10 mL toluene. The filtrate was rotary evaporated to an oil, then flushed and concentrated with 2×30 mL toluene. The toluene flush is required to remove acetic acid which interferes with the next step. The crude hydrazone 3 was used as is in a subsequent reaction.

A small quantity of crude hydrazone 3, prepared as described above, was recrystallized from hexane to provide an analytically pure sample of 3: white crystals, mp 68°–69° C.

$^1$H NMR (CDCl$_3$) δ1.15 (s, 6H, CMe$_2$), 1.65 (s, 3H, N═C—Me), 2.52 (s, 2H, CH$_2$C), 3.58 (s, 3H, CO$_2$Me), 4.39 (s, 2H, CH$_2$N), 5.36 (s, 2H, CH$_2$O), 6.8–7.0 (m, 4H,

O-bearing aromatic), 7.24 (s, 4H, Cl-bearing aromatic), 7.5–8.2 (m, 6H, quinoline H);

$^{13}$C NMR (CDCl$_3$) δ20.0 (q) 26.3 (2, q) 41.4 (s) 49.0 (t), 52.1 (t), 62.5 (q), 72.6 (t), 116.2 (d),, 120.4 (d), 120.7 (d), 127.5 (d), 128.5 (s), 128.86 (d), 128.91 (d), 129.8 (d), 130.7 (d), 131.2 (d), 132.8 (s), 137.8 (d), 139.0 (s), 146.1 (s), 148.5 (s), 154.3 (s), 159.2 (s) 168.7 (s), 178.5 (s).

Step B

Preparation of Indole 4

Method A

1:10 P$_2$O$_5$/MeSO$_3$H in sulfolane (1:1 w/w)

To the crude hydrazone 3 was added anhydrous sulfolane (80 g, water content 70 mg/L) and 1:10 P$_2$O$_5$/MeSO$_3$H solution (80 g). The mixture was aged in the dark for 3 days at 45° C., 1 day at 55° C., and 1 day at 60° C. HPLC analysis at the end of the age showed the following % yield products, based on hydrazine: unreacted hydrazone 3, 1.8%; aniline 6, 5.5; indole 5, 2.3%; indole 4, 77%. The step yields were 91% for hydrazone formation and 85% for indolization.

The reaction was worked-up by cooling to room temperature and adding isopropyl acetate (150 mL). With ice-cooling, 12.5% NaOH (200 mL) was added over a 30 minutes period, keeping the temperature below 40° C. Another 10 mL of 50% NaOH was added to bring the pH to 10. The 2-phase mixture was stirred 10 minutes during which time the mixture turned from greenish-black to reddish-brown. The layers were separated and the organic layer was washed with 3×200 mL water to remove sulfolane. The organic layer was filtered through silica to remove color, then was rotary evaporated to an oil. Methanol (100 mL) was added and the mixture was warmed to 60° C. to dissolve the oil. On cooling thick crystallization occured. The mixture was stirred 3 hours at ambient temperature and 1 hour at 5° C., then filtered and washed with 5×20 mL ice-cold methanol. After drying under vacuum at 50° C., 9.15 g of indole 4 was obtained (69% yield from hydrazine) as a tan solid having a purity of 98 wt %. The major impurity was aniline 6 (1.3%). HPLC assay for components of reaction mixture: Zorbax 25 cm RX column; detection at 220 nm; eluent consisting of 70% acetonitrile/30% 0.1% aq. phosphoric acid; flow, 1.5 mL/min. Retention times: hydrazine 1, 1.6 minutes; aniline 6, 2.5 minutes; indole isomer 5, 6.2 minutes; indole product 4, 6.8 minutes; hydrazone 3, 8.8 minutes.

A small amount of the crude indole 4 was recrystallized from ethanol to provide an analytical sample: white needles, mp 105.5°–106° C.

$^1$H NMR (CDCl$_3$) δ1.26 (s, 6H, CMe$_2$), 2.92 (s, 2H, CH$_2$C) 3.66 (S, 3H, CO$_2$Me), 5.30 (s, 2H, CH$_2$N), 5.43 (s, 2H, CH$_2$O), 6.22 (s, 1H, H-3), 6.8–8.3 (m, 13H, aromatic);

$^{13}$C NMR (CDCl$_3$) δ25.5 (q), 36.4 (t), 43.2 (s), 46.0 (t), 52.0 (q), 72.0 (t), 102.0 (d), 103.7 (d), 110.3 (d), 111.7 (d), 119.3 (d) 126.3 (d), 127.6 (s), 127.7 (d), 128.5 (s), 128.92 (d), 128.94 (d), 129.7 (d), 132.2 (s), 133.0 (s), 136.4 (s), 136.9 (d), 137.5 (s) 147.6 (s), 153.1 (s), 158.9 (s), 177.7 (s).

Anal. Calcd. for C$_{31}$H$_{29}$ClN$_2$O$_3$: C, 72.58; H, 5.70; N, 5.46; Cl, 6.91. Found C, 72.57; H, 5.76; N, 5.45; Cl, 7.00.

Method B

3% P$_2$O$_5$/CH$_3$SO$_3$H in CH$_2$Cl$_2$ (1:2 w/w)

To the crude hydrazone 3, prepared by the method described hereinabove from 1.02 g of the hydrazine 1, was added methylene chloride (13.5 g) and 3% P$_2$O$_5$ in CH$_3$SO$_3$H (6.7 g). The reaction mixture was aged 2 days at ambient temperature, 1 day at 30° C. and 1 day at 35° C. The reaction mixture was then poured into 50 mL of water and the pH of the mixture was adjusted to 10 using 5M NaOH. The organic layer was separated, washed with water, washed with brine and then concentrated to an oil. Methanol (10 mL) was added to the oil and crystallization occurred. The mixture was stirred 2 hours at ambient temperature. The crystals were then filtered and washed with 2 mL methanol and then dried to provide 934 mg of the indole 4 (71% yield overall from the hydrazine 1.)

Method C

10% P$_2$O$_5$/CH$_3$SO$_3$H neat

The crude hydrazone 3 (101 mg, 0.190 mmol), prepared by the method described hereinabove, was added to 1.87 g of 10% P$_2$O$_5$ in methanesulfonic acid. The solution was stirred 22 hours at 23° C. The reaction mixture was dissolved in acetonitrile and assayed by HPLC against a standard of indole 4. The assay indicated the indole 4 was formed in 50% yield and that the ratio of indole 4 to indole 5 was 100:1.

Method D

Polyphosphoric acid in toluene

The crude hydrazone 3 (49 mg, 0.092 mmol), prepared by the method described hereinabove, and polyphosphoric acid (0.90 g) were warmed in 3.15 g of toluene at 80° C. for 3 hours with stirring. HPLC analysis of the reaction mixture at this time indicated that the reaction was complete. The reaction mixture was dissolved in acetonitrile and assayed by HPLC against a standard of indole 4. The assay indicated 17.3 mg of the indole 4 was formed (36% yield) as well as a small amount of indole 5, the ratio of indole 4 to indole 5 being 30:1.

Table 1 illustrates the effects of various acid catalysts and co-solvents on the indolization of hydrozone 3. The isomer ratio listed is the ratio of the 3-unsubstituted indole 4 to the 2-methyl-3-substituted indole 5 from HPLC analysis of the crude reaction.

TABLE 1

| Reagent/Solvent | Temp | Isomer Ratio | % Yield of 4 |
|---|---|---|---|
| MeSO$_3$H | 23 | 100 | 40 |
| 10% P$_2$O$_5$/MeSO$_3$H (neat) | 23 | 100 | 50 |
| 10% P$_2$O$_5$/MeSO$_3$H/TMU (1:1)$^a$ | 55 | 1.0 | — |
| 10% P$_2$O$_5$/MeSO$_3$H/Toluene (1:1) | 55 | 50 | 30 |
| 10% P$_2$O$_5$/MeSO$_3$H/CH$_3$CN (1:1) | 55 | 8 | 65 |
| 10% P$_2$O$_5$/MeSO$_3$H/sulfolane (1:10) | 55 | 1.5 | — |
| 10% P$_2$O$_5$/MeSO$_3$H/sulfolane (1:3) | 55 | 9 | 72 |
| 10% P$_2$O$_5$/MeSO$_3$H/sulfolane (1:2) | 55 | 13 | 77 |
| 10% P$_2$O$_5$/MeSO$_3$H/sulfolane (1:1) | 45 | 40 | 85 |
| 3% P$_2$O$_5$/MeSO$_3$H/CH$_2$Cl$_2$ (1:1) | 45 | 100 | 86 |
| MeSO$_3$H/Sulfolane (1:1) | 55 | 50 | 65 |
| 10% (MeSO$_2$)$_2$O/MeSO$_3$H/sulfolane | 55 | 50 | 65 |
| 10% PPA/MeSO$_3$H/sulfolane (1:1)$^b$ | 55 | 50 | 87 |

$^a$TMU = tetramethylurea
$^b$PPA = polyphosphoric acid

EXAMPLES 2-6

Employing the procedure described in Example 1, method B (wherein the acid catalyst mixture was 3% P$_2$O$_5$ in CH$_3$SO$_3$H and the co-solvent was methylene chloride in a 1:2 w/w ratio), but employing the following hydrazines and methyl ketones, gave the results described in the following table. The isomer ratio listed is the ratio of the 3-unsubstituted indole, analogous to compound 4 in Example 1, to the 2-methyl-3-unsubstituted indole, analogous to compound 5 in Example 1.

Step A

Preparation of the hydrazone 7

Using the procedure described in Example 1, Step A,

| Ex. | R | Methyl Ketone | Isomer Ratio | % Total Yield[a] | Isolated Yield[b] |
|---|---|---|---|---|---|
| 2 | (quinolin-2-ylmethoxy) | H₃C-CO-CH₂-CH(CH₃)₂ | 70:1 | 72 | 68 |
| 3 | " | H₃C-CO-CH₂-CH₂-CO₂Et | 82:18 | 79 | 59 |
| 4 | " | H₃C-CO-CH₂-CH₃ | 86:14 | 76 | 57 |
| 5 | R = i-Pr | H₃C-CO-CH₂-C(CH₃)₂-CO₂Me | 50:1 | 83 | 75 |
| 6 | R = F | H₃C-CO-CH₂-C(CH₃)₂-CO₂Me | 70:1 | 83 | 79 |

[a] Total yield of both indole isomers
[b] % Isolated yield of 3-unsubstituted indole

EXAMPLE 7

Preparation of 2-(2,2-dimethylpropyl)indole

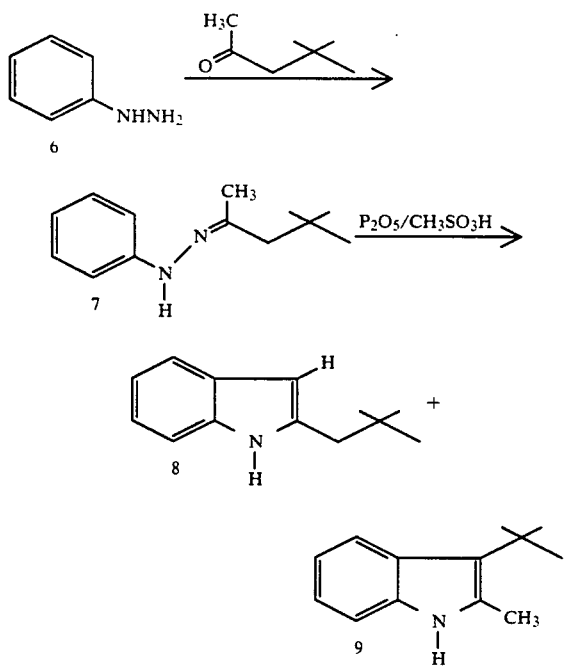

but substituting phenylhydrazine 6 for the hydrazine 1, provided the hydrazone 7 in 90% purity.

¹H NMR (CDCl₃) δ1.05 (s, 9H, CMe₃), 1.92 (s, 3H, N=C—Me), 2.23 (s, 2H, CH₂C), 6.8–7.3 (m, 5H, aromatic).

Step B

Preparation of the indole 8

Hydrazone 7 (90% pure, 1.427 g, 6.30 mmol) and 10% P₂O₅ in CH₃SO₃H (15.0 g) were stirred for 15 hours at 22° C. and 24 hours at 35° C. At the end of the age period the reaction solution was analyzed by HPLC which showed a 90:1 ratio of indole 8:indole 9. The reaction was then poured into a mixture of 50 mL of ice and 50 mL of dichloromethane. After the ice had melted, the layers were separated and the organic layer was washed with sat. NaHCO₃ and then water, then dried over MgSO₄. The material was concentrated to 10 mL and then chromatographed on silica gel using 6:1 hexane:ethyl acetate. The rich cuts were combined and concentrated to provide 0.95 g of indole product 8 (81% yield); m.p. 104°–105° C. (lit. 102°–104° C.).

¹H NMR (CDCl₃) δ1.01 (s, 9H, CMe₃), 2.63 (s, 2H, CH₂C), 6.25 (d, J=2.1 Hz, 1H, H-3), 7.1–7.3 (m, 4H, aromatic), 7.8 ppm (br s, 1H, NH);

¹³C NMR (CDCl₃) δ29.7, 31.9, 43.0, 101.9, 110.4, 119.6, 119.8, 121.0, 128.9, 135.7, 137.6.

EXAMPLES 8-11

Employing the procedure described in Example 7 (wherein the acid catalyst mixture was 10% $P_2O_5$ in $CH_3SO_3H$ and no co-solvent was employed), but employing the following hydrazines and methyl ketones, gave the results described in the following table. The isomer ratio listed is the ratio of the 3-unsubstituted indole, analogous to compound 8 in Example 7, to the 2-methyl-3-unsubstituted indole, analogous to compound 9 in Example 7.

| Ex. | Hydrazine | Methyl ketone | Isomer Ratio | % Total Yield[a] | Isolated Yield[b] |
|---|---|---|---|---|---|
| 8 | 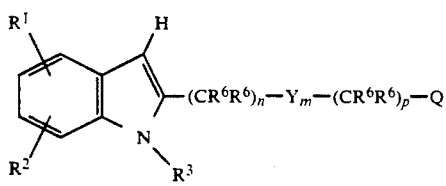 | H₃C-CO-CH₂-CH(CH₃)₂ | 85:15 | 86 | 56 |
| 9 | " | H₃C-CO-CH₂CH₃ | 78:22 | 95 | — |
| 10 | 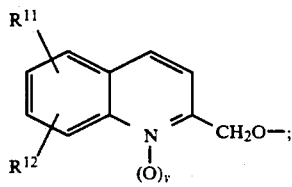 | H₃C-CO-CH₂CH₂CH₃ | 80:20 | 92 | 71 |
| 11 | " | H₃C-CO-CH₂-CH(CH₃)₂ | 90:10 | 85 | 77 |

[a] Total yield of both indole isomers
[b] % Isolated yield of 3-unsubstituted indole

What is claimed is:

1. An improved process for preparing a compound of the formula I:

$$R^1\text{-indole-}(CR^6R^6)_n-Y_m-(CR^6R^6)_p-Q \quad \text{(I)}$$

wherein:

$R^1$ is hydrogen, halogen, lower alkyl, lower alkenyl, lower alkynyl, $-CF_3$, $-CN$, $-NO_2$, $-N_3$, $-C(OH)R^6R^6$, $-CO_2R^7$, $-SR^8$, $-S(O)R^8$, $-S(O)_2R^8$, $-S(O)_2NR^9R^9$, $-OR^9$, $-NR^9R^9$, $-C(O)R^{10}$, $-(CH_2)_rR^{18}$ or

[quinoline structure with $R^{11}$, $R^{12}$, $(O)_v$, $-CH_2O-$]

$R^2$, $R^5$, $R^{11}$ and $R^{12}$ are independently hydrogen, halogen, lower alkyl, lower alkenyl, lower alkynyl, $-CF_3$, $-CN$, $-NO_2$, $-N_3$, $-C(OH)R^6R^6$, $-CO_2R^7$, $-SR^8$, $-S(O)R^8$, $-S(O)_2R^8$, $-S(O)_2NR^9R^9$, $-OR^9$, $-NR^9R^9$, $-C(O)R^{10}$ or $-(CH_2)_rR^{18}$;

$R^3$ is hydrogen or $X^3-R^4$;

$R^4$ is alkyl, alkenyl, $-(CH_2)_uPh(R^5)_2$ or $-(CH_2)_uTh(R^5)_2$;

each $R^6$ is independently hydrogen or lower alkyl, or two $R^6$'s on same carbon atom are joined to form a cycloalkyl ring of 3 to 6 carbon atoms;

$R^7$ is hydrogen, lower alkyl or $-CH_2R^{18}$;

$R^8$ is $-CF_3$ or $R^{13}$;

$R^9$ is hydrogen, $-C(O)R^{10}$, or $R^{13}$;

$R^{10}$ is hydrogen, $-CF_3$, lower alkyl, lower alkenyl, lower alkynyl or $-(CH_2)_rR^{18}$;

$R^{13}$ is lower alkyl or $-(CH_2)_rR^{18}$;

$R^{14}$ is $-(CH_2)_s-C(R^{15}R^{15})-(CH_2)_s-R^{16}$ or $-CH_2-C(O)NR^9R^9$;

$R^{15}$ is hydrogen or lower alkyl;

$R^{16}$ is the radical $W-R^{17}$;

$R^{17}$ is alkyl or $-C(O)R^{20}$;

$R^{18}$ is phenyl substituted with 1 or 2 $R^{19}$ groups;

$R^{19}$ is hydrogen, halogen, lower alkyl, lower alkoxy, lower alkylthio, lower alkylsulfonyl, lower alkylcarbonyl, $-CF_3$, $-CN$, $-NO_2$ or $-N_3$;

$R^{20}$ is alkyl, cycloalkyl, or monocyclic monoheterocyclic ring;

$R^{21}$ is the residual structure of a standard amino acid, or $R^{15}$ and $R^{21}$ attached to the same N can cyclize to form a proline residue;

standard amino acid is: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine or valine;

m is 0 to 1;
n is 1 to 3;
p is 1 to 3 when m is 1;
p is 0 to 3 when m is 0;
r is 0 to 2;
s is 0 to 3;
t is 0 to 2;
u is 0 to 3;
v is 0 or 1;

W is O, S or NR$^9$;
X$^1$ is O or NR$^9$,
X$^2$ is C(O), CR$^6$R$^6$, S, S(O), or S(O)$_2$;
X$^3$ is C(O), CR$^6$R$^6$, S(O)$_2$ or a bond;
Y is X$^1$ or X$^2$;
Q is hydrogen, —CO$_2$R$^7$, —C(O)NHS(O)$_2$R$^8$, —NHS(O)$_2$R$^8$, —S(O)$_2$NHR$^9$—C(O)NR$^9$R$^9$, —CO$_2$R$^{14}$, —C(O)NR$^{15}$R$^{21}$, —CH$_2$OH, or 1H- or 2H-tetrazol-5-yl;

comprising the step of treating the hydrazone compound of the Formula II:

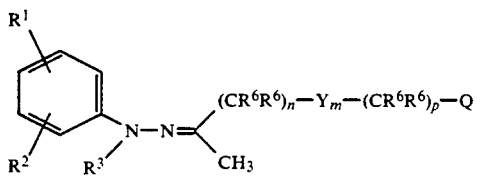

wherein R$^1$, R$^2$, R$^3$, R$^6$, Y, Q, m, n and p are as defined hereinabove;
with a catalyst which is phosphorous pentoxide;
wherein the improvement comprises the presence of a second catalyst which is methane sulfonic acid in a ratio in the range of 2:1 to 40:1 in relation to the phosphorous pentoxide and,
optionally, the additional presence of a co-solvent, in a ratio in the range of 1:1 to 1:10 relative to the mixture of phosphorous pentoxide and methane sulfonic acid.

2. The process of claim 1 wherein a co-solvent is present.

3. The process of claim 2 wherein the co-solvent is dichloromethane.

4. The process of claim 2 wherein the co-solvent is sulfolane.

5. The process of claim 1 wherein a co-solvent is not present.

6. The process of claim 1 wherein each R$^6$ is independently hydrogen, methyl, ethyl, propyl or butyl, or two R$^6$'s on same carbon atom are joined to form a cyclopentyl or cyclohexyl ring; and the remaining substituents are as defined hereinabove for Formula I.

7. An improved process for preparing a compound of the formula Ia:

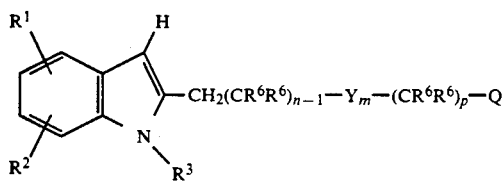

wherein:
R$^1$ is hydrogen, halogen, lower alkyl, lower alkenyl, lower alkynyl, —CF$_3$, —CN, —NO$_2$, —N$_3$, —C(OH)R$^6$R$^6$, —CO$_2$R$^7$, —SR$^8$, —S(O)R$^8$, —S(O)$_2$R$^8$, —S(O)$_2$NR$^9$R$^9$, —OR$^9$, —NR$^9$R$^9$, —C(O)R$^{10}$, —(CH$_2$)$_t$R$^{18}$ or

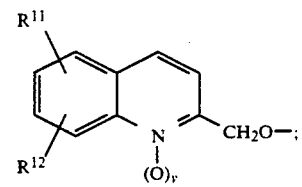

R$^2$, R$^5$, R$^{11}$ and R$^{12}$ are independently hydrogen, halogen, lower alkyl, lower alkenyl, lower alkynyl, —CF$_3$, —CN, —NO$_2$, —N$_3$, —C(OH)R$^6$R$^6$, —CO$_2$R$^7$, —SR$^8$, —S(O)R$^8$, —S(O)$_2$R$^8$, —S(O)$_2$NR$^9$R$^9$, —OR$^9$, —NR$^9$R$^9$, —C(O)R$^{10}$ or —(CH$_2$)$_t$R$^{18}$;

R$^3$ is hydrogen or X$^3$—R$^4$;
R$^4$ is alkyl, alkenyl, —(CH$_2$)$_u$Ph(R$^5$)$_2$ or —(CH$_2$)$_u$Th(R$^5$)$_2$;
each R$^6$ is independently hydrogen or lower alkyl, or two R$^6$'s on same carbon atom are joined to form a cycloalkyl ring of 3 to 6 carbon atoms;
R$^7$ is hydrogen, lower alkyl or —CH$_2$R$^{18}$;
R$^8$ is —CF$_3$ or R$^{13}$;
R$^9$ is hydrogen, —C(O)R$^{10}$, or R$^{13}$;
R$^{10}$ is hydrogen, —CF$_3$, lower alkyl, lower alkenyl, lower alkynyl or —(CH$_2$)$_r$R$^{18}$;
R$^{13}$ is lower alkyl or —(CH$_2$)$_r$R$^{18}$;
R$^{14}$ is —(CH$_2$)$_s$—C(R$^{15}$R$^{15}$)—(CH$_2$)$_s$—R$^{16}$ or —CH$_2$C(O)NR$^9$R$^9$;
R$^{15}$ is hydrogen or lower alkyl;
R$^{16}$ is the radical W—R$^{17}$;
R$^{17}$ is alkyl or —C(O)R$^{20}$;
R$^{18}$ is phenyl substituted with 1 or 2 R$^{19}$ groups;
R$^{19}$ is hydrogen, halogen, lower alkyl, lower alkoxy, lower alkylthio, lower alkylsulfonyl, lower alkylcarbonyl, —CF$_3$, —CN, —NO$_2$ or —N$_3$;
R$^{20}$ is alkyl, cycloalkyl, or monocyclic monoheterocyclic ring;
R$^{21}$ is the residual structure of a standard amino acid, or R$^{15}$ and R$^{21}$ attached to the same N can cyclize to form a proline residue;
standard amino acid is: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine or valine;
m is 0 to 1;
n is 1 to 3;
p is 1 to 3 when m is 1;
p is 0 to 3 when m is 0;
r is 0 to 2;
s is 0 to 3;
t is 0 to 2;
u is 0 to 3;
v is 0 or 1;
W is O, S or NR$^9$;
X$^1$ is O or NR$^9$,
X$^2$ is C(O), CR$^6$R$^6$, S, S(O), or S(O)$_2$;
X$^3$ is C(O), CR$^6$R$^6$, S(O)$_2$ or a bond;
Y is X$^1$ or X$^2$;
Q is hydrogen, —CO$_2$R$^7$, —C(O)NHS(O)$_2$R$^8$, —NHS(O)$_2$R$^8$, —S(O)$_2$NHR$^9$—C(O)NR$^9$R$^9$, —CO$_2$R$^{14}$, —C(O)NR$^{15}$R$^{21}$, —CH$_2$OH, or 1H- or 2H-tetrazol-5-yl;
comprising the step of treating the hydrazone compound of the Formula IIa:

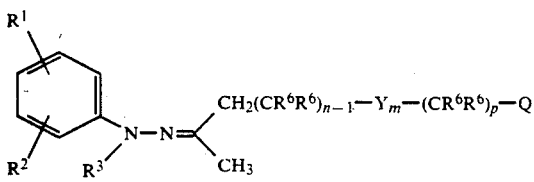

wherein $R^1$, $R^2$, $R^3$, $R^6$, Y, Q, m, n and p are as defined hereinabove;
with a catalyst which is phosphorous pentoxide;
wherein the improvement comprises the presence of a second catalyst which is methane sulfonic acid in a ratio in the range of 2:1 to 40:1 in relation to the phosphorous pentoxide and,
optionally, the additional presence of a co-solvent, in a ratio in the range of 1:1 to 1:10 relative to the mixture of phosphorous pentoxide and methane sulfonic acid.

8. The process of claim 7 wherein each $R^6$ is independently hydrogen, methyl, ethyl, propyl or butyl, or two $R^6$'s on same carbon atom are joined to form a cyclopentyl or cyclohexyl ring; and the remaining substituents are as defined hereinabove for Formula I.

9. The process of claim 7 wherein a co-solvent is present.

10. The process of claim 9 wherein the co-solvent is dichloromethane.

11. The process of claim 9 wherein the co-solvent is sulfolane.

12. The process of claim 7 wherein a co-solvent is not present.

13. The process of claim 9 wherein:
$R^1$ is fluorine, lower alkyl or

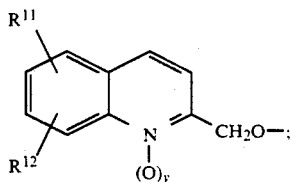

$R^2$, $R^{11}$ and $R^{12}$ are hydrogen;
$R^3$ is $X^3$—$R^4$;
$R^4$ is —$(CH_2)_uPh(R^5)_2$;
$R^5$ is hydrogen or halogen;
m is 0;
n is 1 to 3;
u is 1 in $R^4$;
v is 0;
Q is hydrogen or —$CO_2R^{12}$; and the remaining substituents are as defined hereinabove for Formula I; and the ratio range of phosphorous pentoxide to methane sulfonic acid is 1:9 to 1:35.

14. The process of claim 13 wherein each $R^6$ is independently hydrogen, methyl, ethyl, propyl or butyl, or two $R^6$'s on same carbon atom are joined to form a cyclopentyl or cyclohexyl ring; and the remaining substituents are as defined hereinabove for Formula I.

15. The process of claim 12 wherein:
$R^1$ is fluorine, lower alkyl or $R^2$, $R^{11}$ and $R^{12}$ are hydrogen;
$R^3$ is $X^3$—$R^4$;
$R^4$ is —$(CH_2)_uPh(R^5)_2$;
$R^5$ is hydrogen or halogen;
m is 0;
n is 1 to 3;
u is 1 in $R^4$;
v is 0;
Q is hydrogen or —$CO_2R^{12}$; and the remaining substituents are as defined hereinabove for Formula I; and the ratio range of phosphorous pentoxide to methane sulfonic acid is 1:9 to 1:35.

16. The process of claim 15 wherein each $R^6$ is independently hydrogen, methyl, ethyl, propyl or butyl, or two $R^6$'s on same carbon atom are joined to form a cyclopentyl or cyclohexyl ring; and the remaining substituents are as defined hereinabove for Formula I.

* * * * *